United States Patent [19]

Guest

[11] Patent Number: 4,795,439
[45] Date of Patent: Jan. 3, 1989

[54] SPIRAL MULTI-LUMEN CATHETER

[75] Inventor: Robert L. Guest, Athens, Tex.

[73] Assignee: Edward Weck Incorporated, Princeton, N.J.

[21] Appl. No.: 177,820

[22] Filed: Apr. 8, 1988

Related U.S. Application Data

[63] Continuation of Ser. No. 871,354, Jun. 6, 1986, abandoned.

[51] Int. Cl.$^4$ ............................................. A61M 5/00
[52] U.S. Cl. ................................... 604/43; 604/264; 604/280; 138/115
[58] Field of Search .................. 604/43–45, 604/48, 49, 51, 53, 54, 93, 94, 96, 102, 129, 173, 257, 258, 264, 266, 268, 270, 275, 280–284; 138/111, 115–117; 128/343, 674; 264/177.14, 177.17, 209.1, 209.2, 209.3, 154–156, 295, 285

[56] References Cited

U.S. PATENT DOCUMENTS

| | | | |
|---|---|---|---|
| 547,047 | 10/1895 | Thorton et al. | 604/275 |
| 1,876,444 | 9/1932 | Babb | 264/209.3 |
| 2,230,218 | 2/1941 | Asche | 604/43 |
| 2,743,960 | 5/1956 | Kamin | 138/115 |
| 2,802,530 | 8/1957 | Kaufman | 264/156 |
| 3,279,501 | 10/1966 | Donald | 264/209.2 |
| 3,394,705 | 7/1968 | Abramson | 604/43 |
| 3,815,608 | 6/1974 | Spinosa et al. | 604/105 |
| 3,864,446 | 2/1975 | Maroschak | 264/209.3 |
| 3,999,554 | 12/1976 | Kim et al. | 604/264 |
| 4,072,146 | 2/1978 | Howes | 604/158 |
| 4,139,012 | 2/1979 | Zahorsky | 604/268 |
| 4,402,684 | 9/1983 | Jessup | 604/43 |
| 4,406,656 | 9/1983 | Hattler et al. | 604/43 |
| 4,501,580 | 2/1985 | Glassman | 604/43 |

FOREIGN PATENT DOCUMENTS

| | | | |
|---|---|---|---|
| 0462432 | 1/1914 | France | 604/282 |
| 0564832 | 1/1924 | France | 604/280 |

Primary Examiner—Stephen C. Pellegrino
Assistant Examiner—Ralph Lewis
Attorney, Agent, or Firm—Lawrence S. Levinson; Robert E. Lee, Jr.

[57] ABSTRACT

An improved multi-lumen catheter having lumens which do not extend in a straight line down the length of the catheter is disclosed. The twisting of the catheter provides that side holes which extend into the lumens of the catheter are not aligned in a straight line. Accordingly, when the catheter is inserted into a patient's vessel, the side holes cannot be aligned in a manner which causes all of the side holes of a particular lumen to be occluded by the wall of the patient's vessel.

A catheter of the type disclosed can be manufactured by an extrusion process in which the catheter is twisted during the extrusion, or by heating a non-twisted catheter and then twisting it in order to impart an appropriate twist therein.

1 Claim, 1 Drawing Sheet

U.S. Patent    Jan. 3, 1989    4,795,439
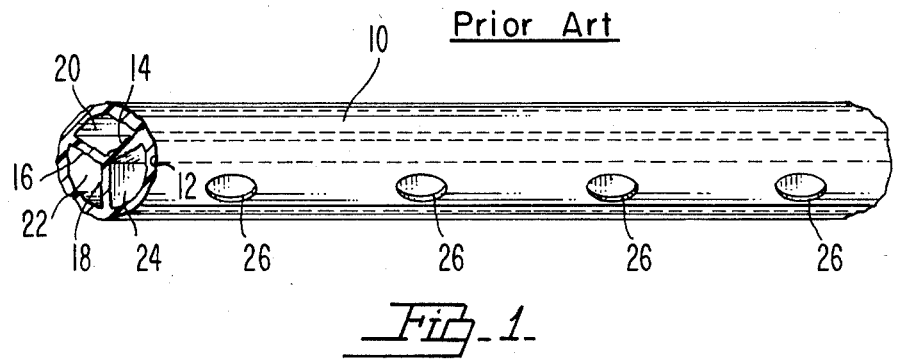
_Fig_1_
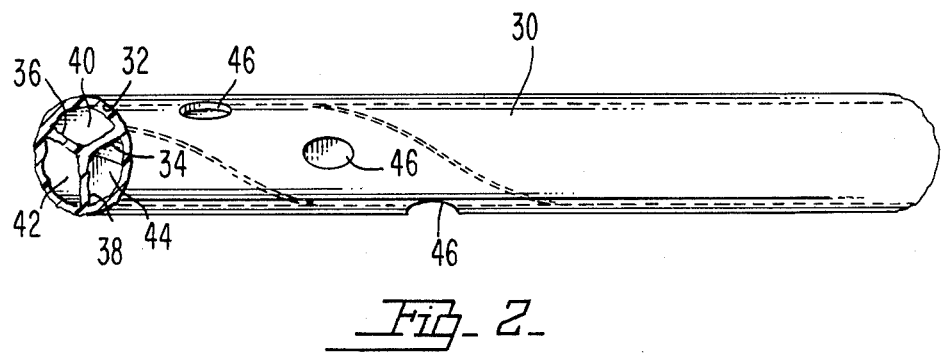
_Fig_2_

SPIRAL MULTI-LUMEN CATHETER

This is a continuation of co-pending application Ser. No. 871,354 filed on June 6, 1986 now abandoned.

BACKGROUND OF THE INVENTION

The present invention relates to catheters of the type used in medical applications. In particular, the invention relates to multi-lumen catheters.

A multi-lumen catheter is used in medical applications which require more than one lumen for introducing medication or other fluids into a patient and/or removing blood from a patient at the same time. Typically, multi-lumen catheters, when viewed in cross-section, appear to be circular and to have lumen walls which extend radially from the center of the circle.

Accordingly, a triple lumen catheter would appear in cross-section like a pie which has been cut into three portions (which are not necessarily equal in size). This appearance results from the fact that catheters are typically manufactured out of plastic by an extrusion process. The distal end of a multi-lumen catheter is typically sealed, and side holes are formed near the distal end into each of the lumens. As a result, the side holes of any one of the lumens are all within a given segment of the arc defined by the interior walls and the outside circumference of the catheter. As a result of this configuration, it is possible that the side holes of one lumen can be wholly or partially occluded by the interior wall of a patient's vessel when the catheter has been inserted.

SUMMARY OF THE INVENTION

The present invention is a multi-lumen catheter having side holes which extend through the exterior catheter wall into at least one of the lumens of the catheter. Either during fabrication of the multi-lumen catheter or thereafter, the catheter is processed to impart a spiral whereby the side holes which enter the respective lumens are not aligned along the length of the catheter.

BRIEF DESCRIPTION OF DRAWINGS

In the Drawing:

FIG. 1 is a perspective view of a catheter made in accordance with the prior art; and FIG. 2 is a side view of a catheter made in accordance with the present invention.

DETAILED DESCRIPTION OF THE PREFERRED EMBODIMENT

Referring generally to FIG. 1, a portion of a multi-lumen catheter 10, or the type heretofore known, is shown. The multi-lumen catheter 10 is comprised of an exterior wall 12 and a series of interior walls 14, 16, 18 which define three lumens 20, 22, 24. The interior walls 14, 16, 18 extend down the length of the catheter 10 longitudinally as a result of the method by which catheters are typically manufactured, namely by extrusion. As a consequence of this manufacturing process, side holes 26, which extend into one of the lumens 24 are all aligned along the length of the catheter 10. Consequently, if a catheter of this type is placed into a patient's vein, it is possible for all of the side holes 26 of one of the lumens 20, 22, 24 to be pressed along the side of the patient's vein, thereby wholly or partially occluding the side holes 26, and preventing the catheter 10 from acting efficiently.

Referring generally to FIG. 2, a catheter 30 made in accordance with the present invention, is shown. The catheter 30 includes an exterior side wall 32 and interior side walls 34, 36, 38 which define lumens 40, 42, 44. The catheter 30 of the present invention, however, is manufactured in accordance with a process whereby the catheter 30 is twisted in the course of its manufacture. Accordingly, the side holes 46 which enter into one of the lumens 40 are not formed in a straight line along the outside wall 32 of the catheter 30. Instead, the side holes 46 which enter into a particular lumen 40 spiral about the catheter 30, thereby preventing occlusion of the side holes 46 as a result of specific placement of the catheter 30 in the patient's vessel.

The spiral of the interior walls 34, 36, 38 of the catheter 30 can be accomplished by twisting the catheter tubing at the time it is originally extruded or by a similar, secondary process which involves heating and twisting the tubing of the catheter 30 after it has been extruded. As will be obvious to those skilled in the art, it is only necessary for the distal portion of the catheter, i.e., the portion containing the side holes 46, to be subjected to the twisting of the present invention.

Catheters manufactured in accordance with the present invention will not exhibit occlusion of a particular lumen as a result of the particular placement of a catheter within the patient. Accordingly, they provide performance which is superior to that of the catheter 10 of the prior art.

I claim:

1. An improved multi-lumen catheter of the type comprising a plastic tube having an outer cylindrical surface and a longitudinal axis, which plastic tube has been divided into a plurality of lumens by generally radially extending interior walls which intersect said outer cylindrical surface, each lumen rotating only at its distal end along a portion of its length about the longitudinal axis of the tube in a spiral-like manner, there being side holes which enter into at least one of the lumens formed thereby at the rotated distal end only

* * * * *